United States Patent [19]

Castro et al.

[11] 4,172,705

[45] Oct. 30, 1979

[54] PROCESS AND APPARATUS FOR SULFUR ANALYSIS

[75] Inventors: James M. Castro, Fremont; Joshua A. Duberman, Santa Clara; Robert T. Moore, Palo Alto, all of Calif.

[73] Assignee: Envirotech Corporation, Menlo Park, Calif.

[21] Appl. No.: 895,686

[22] Filed: Apr. 12, 1978

[51] Int. Cl.$^2$ ............................................. G01N 31/12
[52] U.S. Cl. .................................. 23/230 PC; 55/71; 55/73; 55/74; 422/80
[58] Field of Search ................. 23/253 PC, 230 PC; 55/71, 74, 73; 422/78, 80

[56] References Cited

U.S. PATENT DOCUMENTS

| 3,598,531 | 8/1971 | Bremanis | 23/230 PC |
| 4,081,247 | 3/1978 | Neti et al. | 23/253 PC |

OTHER PUBLICATIONS

Burke, "Rapid Combustion Method for the Determination of Sulfur in Nickel-, Iron-, and Copper-Base Alloys;" Anal. Chem.; vol. 39; No. 14; Dec. 1967, pp. 1727–1731.
Bandi et al.; Determination of Trace Amounts of Sulfur in Iron & Steel by Combustion–Coulometry; Anal. Chem.; vol. 38; No. 11; Oct. 1966; pp. 1485–1489.
Larsen et al.; Separation and Determination of Microgram Amounts of Sulfur; Anal. Chem.; vol. 31; No. 9; Sep. 1959; pp. 1596–1597.
Burke et al.; Combustion–Spectrophotometric Method for Determination of Trace Quantities of Sulfur in Metals; Anal. Chem.; vol. 34; No. 13; Dec. 1962; pp. 1747–1751.
Brochure SM-716-094750 describing Dohrmann DC 60 carbon monitor.

Primary Examiner—Arnold Turk
Attorney, Agent, or Firm—William S. Bernheim; John J. Morrissey

[57] ABSTRACT

Process and apparatus for micro-coulometric determination of sulfur in hydrocarbon samples in which interference of chlorine and oxides of nitrogen is minimized. The process comprises the steps of oxidizing the sample, scrubbing the oxidized sample with a tin-containing agent and coulometrically titrating the sample thereafter.

7 Claims, No Drawings

PROCESS AND APPARATUS FOR SULFUR ANALYSIS

BACKGROUND

This invention relates to an oxidative method for microcoulometric determination of sulfur in hydrocarbons.

The presence of chlorine in concentrations in excess of 1 ppm and nitrogen in excess of 0.1 ppm may interfere in the iodometric determination of sulfur in petroleum and chemical products using the iodometric ASTM Method of Test for Sulfur in Petroleum Gas by Oxidative Microcoulometry (D 3246-76) and similarly in the method for sulfur in petroleum liquid (ASTM D 3120-75) or their equivalents. In the case of nitrogen, the extent of such interference is dependent on the type of nitrogen compounds as well as the amount present.

The interference results from oxidation of nitrogen to oxides of nitrogen and from oxidation of organic and inorganic chlorides to elemental chlorine, each of which reacts with potassium iodide in the iodometric titration to liberate iodine. Sulfur is oxidized in the method to sulfur dioxide which is measured by the consumption of iodine in the titration. Therefore, the effect of the presence of nitrogen and chlorine is to cause low, or even negative results. Since chlorine, and especially nitrogen, are commonly associated with sulfur in petroleum products, petrochemicals, and chemicals, this interference constitutes a severe limitation of the above methods.

Efforts have been made to overcome such interference. U.S. Pat. No. 3,598,531 to Bremanis describes a method whereby alkali metal azides are added to a titration solvent. Apparently, the azides react preferentially with the chlorine and the harmful oxides of nitrogen before such chlorine and oxides of nitrogen can react with the potassium iodide. Although azide addition appears to improve the sensitivity and precision of the measurement for sulfur according to the ASTM method, interference still prevents accurate measurements of sulfur below 1 ppm.

It is an object of this invention to provide an improved method for determining sulfur as sulfur dioxide in petroleum and chemical products. More particularly, an object is to provide a way of overcoming nitrogen and chlorine interference in the methods of sulfur determination involving microcoulometry. Yet another object is to provide a method for determining sulfur at lower concentrations than heretofore possible with conventional microcoulometric techniques.

SUMMARY OF THE INVENTION

It has been found that sulfur concentration can be determined at levels from 10 ppb up to 10 ppm in gas or liquid samples including a nitrogen concentration up to 100 ppm and a chlorine concentration up to 200 ppm. Such determinations are made by modifying the above-described ASTM oxidative microcoulometric methods for sulfur determination. The ASTM methods include an oxidation step followed by a titration step; those methods are modified according to the invention by addition of a scrubbing step between the oxidation step and titration step. In the scrubbing step the products of the oxidation step are contacted with metallic tin. It is believed that the tin reacts with the chlorine and such oxides of nitrogen as would otherwise interfere to form tin-containing compounds while simultaneously not reacting with the sulfur dioxide.

DETAILED DESCRIPTION OF PREFERRED EMBODIMENT

To summarize the above-discussed ASTM method for petroleum gas, a sample of hydrocarbon containing gas is injected into a combustion tube maintained at about 800° C. Through the tube is passed a stream of gas containing about 80 percent oxygen and 20 percent inert gas (for example, nitrogen, argon). Oxidative pyrolysis occurs in the tube whereby sulfur in the sample is converted to sulfur dioxide gas which is then passed into a titration cell where titration of the sulfur dioxide in the oxidized sample is accomplished. More specifically, any sulfur dioxide in the oxidized sample reacts, in the electrolyte in the titration cell, with triiodide ions present in the electrolyte. The triiodide thus consumed is replaced by the coulometric action of the cell, and the current required to effect this is a measure of the sulfur present in the sample injected.

According to the present invention, the above-described method is improved by locating a bed of granular tin between the combustion tube and the titration cell. Preferably, the tin is maintained at a temperature which prevents condensation of water from the gas stream therein; normally, a temperature above 100° C. is sufficient for this purpose. Residence times of the oxidized sample in the bed of 0.1 to 100 milliseconds are suitable.

Our improved process therefore includes the steps of: (a) pyrolytically oxidizing a sample, (b) contacting the products of the oxidation with tin, and (c) coulometrically titrating the contacted products.

In practicing our improved method, accuracy of the sulfur determination has been the higher of 10 ppb or 2 percent of the measured amount over the range of 10 ppb (compared with the earlier limit of 1 ppm) up to 10 ppm. Further in practicing our improved method, concentrations of nitrogen and chlorine up to 100 ppm and 200 ppm, respectively, can be tolerated before interference occurs. For measuring samples containing higher concentrations of nitrogen or chlorine, the sample can be diluted to bring such concentrations within the tolerances (i.e., within 100 and 200 ppm, respectively). And this is because of the new much lower concentrations at which sulfur can be measured.

As mentioned above, the preferred scrubbing material is metallic tin. Other metals such as silver, lead, copper and zinc were tested but proved unsatisfactory because they did not show the necessary selectiveness for reacting with chlorine and interfering oxides of nitrogen in preference to reacting with sulfur dioxide.

Tin suitable for practicing our improved method is available from the Baker Chemical Company of Phillipsburg, New Jersey, and is described as tin, granular 20 mesh (Baker Analyzed Reagent). A typical lot analysis of this tin reads in part as follows: 102.9 percent tin by EDTA titration, 0.01 percent iron (by AAS), 0.04 lead (by AAS), 0.006 percent zinc (by AAS), and 0.0008 copper (by AAS). Higher concentrations of the non-tin metals (e.g., lead, zinc, etc.) in the scrubbing material may interfere with the sulfur determination by reacting with the sulfur dioxide.

In practice, we prefer the following process for preparing the tin for its function as a scrubbing material. This procedure consists of passing a 300 microliter "conditioning" sample through the sampling apparatus where the sample contains 200 ppm chlorine, 100 ppm nitrogen and 10 ppm sulfur. Preferably this conditioning sample is injected at a rate of from 0.2 to 0.5 microliters per second; this conditioning process normally takes about 10 minutes.

We claim:

1. A method for iodometrically determining trace sulfur concentrations in a hydrocarbon sample, said method comprising the sequential steps of:
   (a) pyrolytically oxidizing said hydrocarbon sample in a combustion device to convert sulfur in said sample to sulfur dioxide;
   (b) passing the products of the oxidation step, including sulfur dioxide, from said combustion device to a titation cell via a scrubbing device containing a scrubbing agent, said scrubbing agent consisting essentially of tin to scrub out chlorine and oxides of nitrogen without substantially reacting with sulfur dioxide; and
   (c) iodometrically titrating said products of said oxidation step, except for the chlorine and oxides of nitrogen removed by said scrubbing agent, to determine the concentration of sulfur dioxide whereby the concentration of sulfur in said sample can be coulometrically measured.

2. The method of claim 1 wherein said scrubbing device comprises a bed formed of granular tin.

3. The method of claim 1 wherein said scrubbing agent is maintained at a temperature above 100° C.

4. The method of claim 1 wherein the products of the oxidation step are retained in said scrubbing device for a residence time of from 0.1 to 100 milliseconds.

5. In an apparatus for iodometrically determining sulfur concentration in a hydrocarbon sample, wherein said apparatus comprises a combustion device in which oxidative pyrolysis of said sample can occur whereby sulfur-containing components of said sample are converted to sulfur dioxide, means for passing products of said oxidative pyrolysis including sulfur dioxide from said combustion device to a titration cell, and a titration cell for iodometrically determining sulfur dioxide, the improvement wherein said means for passing products includes a scrubbing means containing a scrubbing agent consisting essentially of tin for selectively reacting with chlorine and oxides of nitrogen without substantially reacting with sulfur dioxide so as to substantially preclude passage of chlorine and oxides of nitrogen without substantially preventing passage of sulfur dioxide into said titration cell.

6. The apparatus of claim 5 further comprising means for maintaining said scrubbing agent at a temperature above 100° C.

7. The apparatus of claim 5 wherein said scrubbing agent is in the form of a bed of granular tin.

* * * * *